(12) United States Patent
Doll et al.

(10) Patent No.: US 6,206,838 B1
(45) Date of Patent: Mar. 27, 2001

(54) AUTOLOADER AND SKIN TESTING SYSTEM

(75) Inventors: Joseph L. Doll, Patterson; Ralph E. Reese, Blowing Rock; William White, Jr., Lenoir, all of NC (US)

(73) Assignee: Greer Laboratories, Inc., Lenoir, NC (US)

( * ) Notice: Subject to any disclaimer, the term of this patent is extended or adjusted under 35 U.S.C. 154(b) by 0 days.

(21) Appl. No.: 09/629,674

(22) Filed: Aug. 1, 2000

Related U.S. Application Data (63) Continuation of application No. 09/148,458, filed on Sep. 4, 1998, now Pat. No. 6,095,988.

(51) Int. Cl.⁷ .................................................. A61B 5/00
(52) U.S. Cl. ............................................................. 600/556
(58) Field of Search ............................ 600/556; 206/142, 206/143, 153, 161, 168

(56) References Cited

U.S. PATENT DOCUMENTS

| | | |
|---|---|---|
| D. 247,822 | 5/1978 | Hein et al. . |
| 2,522,309 | 9/1950 | Simon . |
| 3,289,670 | 12/1966 | Krug et al. . |
| 3,556,080 | 1/1971 | Hein . |
| 4,237,906 | 12/1980 | Havstad et al. . |
| 4,270,548 | 6/1981 | Brennan . |
| 4,292,979 | 10/1981 | Inglefield, Jr. et al. . |
| 4,304,241 | 12/1981 | Brennan . |
| 4,448,452 | 5/1984 | Wood . |
| 4,453,926 | 6/1984 | Galy . |
| 4,711,247 | 12/1987 | Fishman . |
| 4,759,755 | 7/1988 | Hein et al. . |
| 4,878,900 | 11/1989 | Sundt . |
| 5,027,826 | 7/1991 | Fishman . |
| 5,647,371 | 7/1997 | White, Jr. et al. . |
| 5,671,753 | 9/1997 | Pitesky . |
| 5,673,705 | 10/1997 | Pitesky . |
| 5,692,518 | 12/1997 | Baker et al. . |
| 5,735,288 | 4/1998 | Fishman . |

Primary Examiner—Cary O'Connor
Assistant Examiner—Pamela L. Wingood
(74) Attorney, Agent, or Firm—Alston & Bird LLP (57) ABSTRACT

There is provided an autoloader apparatus and skin testing system for rapidly loading a multi-headed applicator used for epicutaneous application of biological testing agents, while at the same time, effectively inhibiting cross contamination of testing agents during loading and removal of the applicator. The autoloader apparatus includes a plurality of reservoirs for storing testing agents therein. Each reservoir includes a collar defining an open top. The autoloader apparatus further includes a receptacle having first and second surfaces defining a plurality of apertures therethrough for at least partially receiving the collars of the reservoirs. The skin testing system includes an applicator and an autoloader. The applicator has a plurality of picks for sealably engaging the open tops of the reservoirs of the autoloader to enable each pick to be loaded with an effective amount of testing agent. The testing agents are epicutaneously deposited by piercing the patient's skin with each pick to a predetermined depth and observing the pierced skin for response to the testing agent.

16 Claims, 5 Drawing Sheets

AUTOLOADER AND SKIN TESTING SYSTEM

CROSS-REFERENCE TO RELATED APPLICATIONS

This application is a continuation of U.S. application Ser. No. 09/148,458, filed Sep. 4, 1998 now U.S. Pat. No. 6,095,988.

FIELD OF THE INVENTION

The present invention relates to an apparatus for use in connection with skin tests for allergic or other diagnostic reasons. More particularly, the present invention relates to an autoloading apparatus and skin testing system for rapidly loading a multi-headed applicator used for epicutaneous application of biological testing agents, which effectively inhibits cross contamination of testing agents during loading and removal of the applicator.

BACKGROUND OF THE INVENTION

Diagnosis of allergies has relied upon a number of techniques for introducing various biological substances to the epidermis or dermis. In a widely accepted testing method for allergies and other immunologic conditions—the skin test—various biologicals, such as aeroallergens, food allergens, and other substances are applied by abrading, cutting or puncturing the epidermal skin layer and contacting the liquid allergenic extract or the like with the exposed skin tissue. The test areas are often on the back or arm of the patient and the tests normally cause some discomfort. If the patient is allergic to a particular biological substance which is applied, histamine or a histamine substance will be released by the affected tissue resulting in redness and swelling in that area. The specific test sites are then compared to a control test site to visually determine if the patient is allergic to a particular test substance.

The skin tests may be performed one test at a time with each allergenic extract being loaded onto a scarifier or pick and applied to the skin. An example of a device for applying single tests is shown in U.S. Pat. No. 4,270,548. As it is desirable to speed up the testing process, devices for performing multiple tests simultaneously were developed. One such skin testing device that is widely used is the applicator disclosed in U.S. Pat. No. 3,556,080 to Hein which discloses a plastic applicator having an elongate handle from which extend curved connecting legs, each one of which terminates in a pressure puncture head having a cluster of sharp points. The method of using the Hein multi-headed applicator is to place the applicator upside down with the rigid handle being supported in a holder, such as described in Hein's U.S. Design Pat. No. 247,822. Each of the pressure puncture heads or picks is then individually loaded with a testing substance by the doctor or nurse. Once the puncture heads are individually loaded, the applicator is grasped by the elongate handle and then applied to the skin in a manner such that each puncture head can penetrate the surface of the skin. Using this method requires loading each puncture head individually, which is laborious and can take a considerable amount of time.

An early form of a multi-headed skin test applicator is disclosed in U.S. Pat. No. 2,522,309 to Simon. In the Simon patent, the applicator comprises test covers (handles) having needles attached thereto that are placed over a plurality of allergen containing wells in a manner to allow the needles to enter the fluid. Each well must be filled with the desired testing substance, which is laborious and time consuming. Also, any unused testing substance must be discarded so that the wells may be cleaned and sterilized prior to storage. The covers fit snugly over the wells in a sealing relationship. When the multi-headed applicator is removed from the wells with a spiral motion, the needles touch the sides of the wells to remove excess allogenic extract. The loaded multi-headed applicator is then used in the normal manner.

The desire to simplify and speed-up allergy testing procedures has led to the development of a number of other multi-headed skin test applicators. The patent to Galy, U.S. Pat. No. 4,453,926, provides a multi-headed scarifying device for simultaneously performing a plurality of skin tests. The device has a clustered group of points that are contained in a hermetically sealed envelope with the envelope containing an active liquid substance into which the cluster points are immersed. To operate the Galy device, one must individually remove each envelope tab, which is not only time consuming, but provides an opportunity for the testing substances to drip from the exposed heads while the remaining envelopes are being removed.

U.S. Pat. No. 3,289,670 to Krug, et al. describes a multi-headed device for simultaneously performing a plurality of skin tests. The device includes a structure having a flat upper surface defining a plurality of wells. The device also includes a reusable abrading unit having multiple skin abrading members. The abrading unit fits on top of the structure so that each abrading member fits into a corresponding well and is immersed in the liquid testing substance. When the tests are performed, the abrading unit is removed from the structure and applied to the patient in the normal manner. Repeated removal and replacement of the abrading unit during a series of tests, however, can result in testing substances dripping from the individual abrading members or otherwise becoming deposited on the surface of the structure and inside the adjacent wells, thus contaminating the testing substances in the wells. In the event the testing substances become contaminated, any subsequent skin tests could be inaccurate and result in an incorrect diagnosis.

The present invention overcomes the disadvantages of the prior art by providing an autoloading apparatus and skin testing system for rapidly loading a multi-headed skin testing applicator with biologicals or other testing agents, while at the same time, effectively inhibiting the cross contamination of testing agents.

SUMMARY OF THE INVENTION

It has been found that the autoloading apparatus and skin testing system of the present invention enables the user to rapidly and efficiently load a multi-headed skin testing applicator used for epicutaneous application of biologicals or other test agents, while effectively inhibiting cross contamination of testing agents. The autoloading apparatus of the present invention provides a plurality of reservoirs for storing testing agents. The testing agents can include allergens such as tree allergens, mold allergens, grass allergens, ragweed allergens, dust, epidermals, and weed allergens. Each reservoir has a collar defining an open top. The reservoirs preferably include means for labelling each reservoir to identify the corresponding testing agent stored therein.

The autoloading apparatus also includes a receptacle having first and second surfaces defining a plurality of apertures therethrough. Each aperture removably receives at least a portion of the collar of one of the reservoirs. In one preferred embodiment, the collar of the reservoirs projects above the first surface of the receptacle thereby inhibiting cross contamination of testing agents between reservoirs. The outer surface of each collar is preferably threaded, as is the surface of each aperture so that the aperture can threadedly receive the collar of the corresponding reservoir.

In a second preferred embodiment, the receptacle again includes first and second surfaces defining a plurality of apertures therethrough. The first surface of the receptacle defines at least one recess that defines a rim around at least a portion of each of the plurality of apertures. In this embodiment, the apertures preferably include an aperture-reduction member disposed between the first and second surfaces. The rims around the apertures inhibit cross contamination of testing agents between the reservoirs. The recess preferably defines at least one rib to restrict the flow of excess testing agents deposited within the recess.

The skin testing system includes an autoloading apparatus and an applicator. In one preferred embodiment, the applicator has first and second surfaces. The second surface of the applicator has a plurality of picks. Each pick has at least one skin piercing epidermal point and is capable of carrying a load of testing agent. The applicator is preferably formed with a predetermined curvilinear configuration. Likewise, the receptacle is also formed with a curvilinear configuration that corresponds to the curvilinear configuration of the applicator thereby providing positive reference orientation between the applicator and the receptacle.

In a second preferred embodiment, the applicator includes an applicator handle and at least one applicator test strip storable separately from the applicator handle. The test strip has a plurality of heads or picks. Each pick has at least one skin piercing epidermal point and is capable of carrying a load of testing agent. The applicator preferably includes complimentary coupling means on the test strip and on the applicator handle to permit the handle to operatively pick up and releasably hold the test strip when the test strip is used.

It is therefore an object of the present invention to provide an autoloading apparatus and skin testing system for simultaneously performing a plurality of skin tests to determine the allergic response to the application of biological testing agents to the scratched skin.

Another object of the present invention is to provide an autoloading apparatus and skin testing system for effectively storing testing agents for subsequent loading of a multi-headed applicator used in performing a skin test.

Yet another object of the present invention is to provide an autoloading apparatus skin testing system for rapidly loading a multi-headed applicator used for performing skin tests with biological testing agents, while at the same time, effectively inhibiting cross contamination of the testing agents.

BRIEF DESCRIPTION OF THE DRAWINGS

Other objects, features and advantages of the invention will be apparent from the detailed description of the invention when taken in conjunction with the accompanying drawings, in which.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete and will fully convey the scope of the invention to those skilled in the art. Like numbers refer to like elements throughout.

Figures 1, 2:
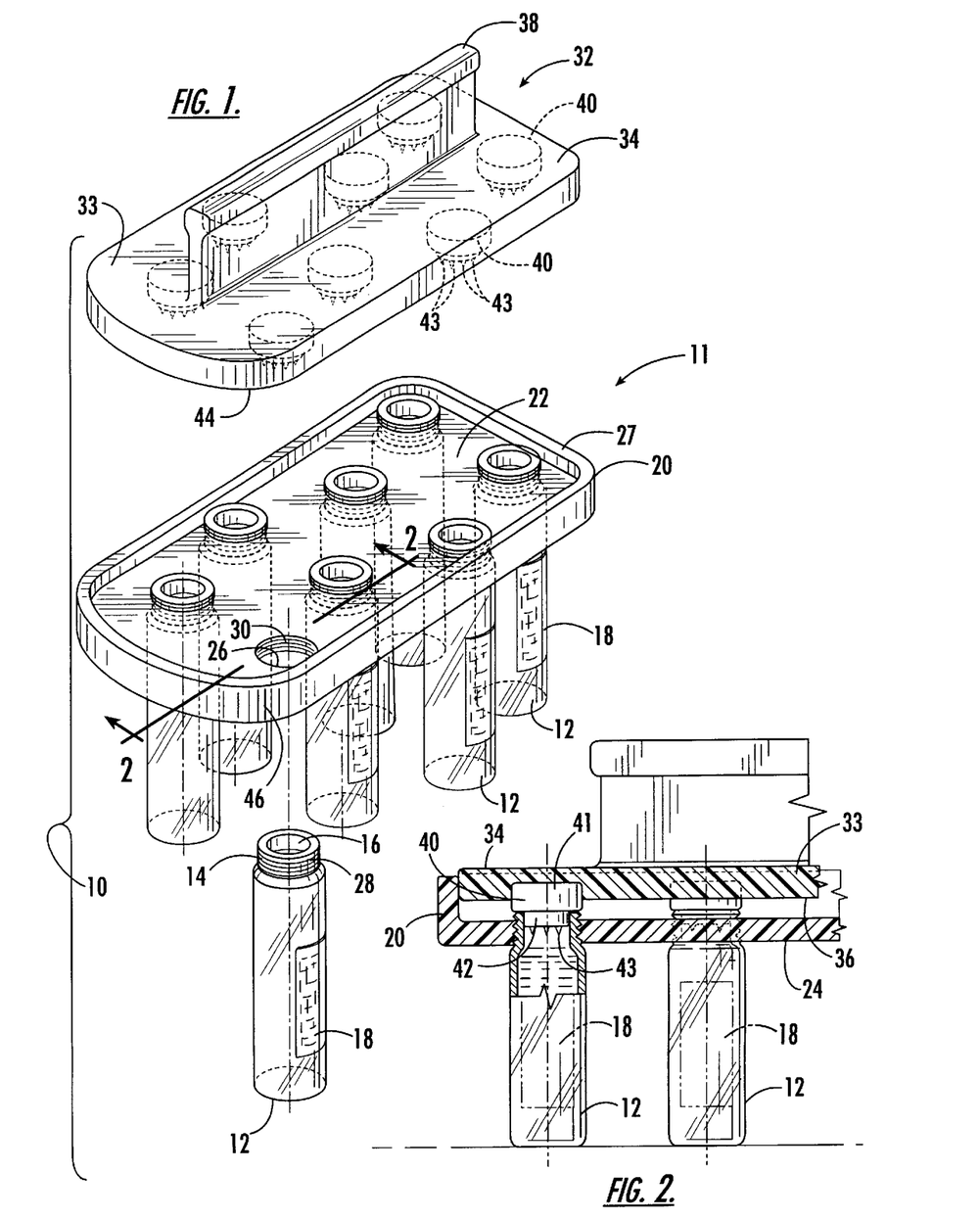
FIG. 1 is a partial exploded perspective view illustrating one embodiment of the skin testing system of the present invention including an autoloading apparatus having a receptacle and a plurality of reservoirs and a multi-headed skin testing applicator.
FIG. 2 is a fragmentary cross sectional view illustrating the skin testing system of FIG. 1.

Referring now to the drawings, and in particular to FIG. 1, there is shown a skin testing system 10 according to one preferred embodiment of the present invention. The skin testing system includes an autoloader 11 and a skin testing applicator 32. The autoloader includes a plurality of reservoirs or containers 12 for storing testing agents therein. The testing-agent containers are preferably cylindrical in configuration and constructed of a nonreactive and durable material, such as an extruded or injection molded plastic or tempered glass. The containers may be pre-filled with testing agents and sealed using a removable cap or top (not shown). Each testing-agent container has a collar 14 defining an open top 16. The container preferably includes a means for labelling the container to identify the testing agent stored therein. The labelling means may include a pressure-sensitive label 18 having a pre-printed description or a label having an exterior surface upon which the user can record an identification for the testing agent.

The testing agents can include allergens such as tree allergens, mold allergens, grass allergens, ragweed allergens, dust, epidermals, and weed allergens. The testing agents are typically categorized into groups. For example, inhalant or aeroallergens are divided into seven or eight groups depending on the antigens found in a particular geographical location. Food antigens may also be divided into groupings. The preferred groupings of inhalant antigens include extracts of pollens, molds, dust, epidermals, insects and foods. The antigens may be used in either an aqueous form or a glycerin-saline base. For trees, weeds, and grasses, the preferred concentration is 50 grams/liter (g/l). For mold, epidermals and house dust, the preferred concentration is 100 g/l. Additionally, control test substances of the particular diluent used and one of histamine are generally used for the purpose of insuring against false-positive reactions.

The autoloader 11 shown in FIG. 1 also includes a receptacle 20 having first and second surfaces 22, 24 defining a plurality of apertures 26 therethrough. The apertures are preferably staggered in two groups along the length of the receptacle. As illustrated in FIG. 1, the receptacle may include two groups of four staggered apertures, each group extending along opposite sides of the receptacle for a total of eight apertures. However, it should be appreciated that the number of apertures can be as few as two or as many as desired and still be within the scope of the teachings of the present invention. The receptacle can be fabricated from an extrudable or injection molded plastic. Each aperture removably receives at least a portion of the collar 14 of one of the testing-agent containers 12. The outer surface 28 of each collar is preferably threaded, as is the inner surface 30 of each aperture, so that each aperture can threadedly receive the collar of the corresponding testing-agent container. Advantageously, once the containers are secured within the apertures of the receptacle, the receptacle and containers form a free-standing autoloader unit, with the containers supporting the receptacle in the upright position.

In one preferred embodiment of the autoloader 11, the collar 14 of each corresponding testing-agent container 12 projects above the first surface 22 of the receptacle 20 to thereby inhibit cross contamination of the testing agents between the containers during use of the skin testing device 10. In this embodiment, the receptacle also includes a peripheral lip 27 to contain any testing agent that has dripped onto the first surface or topside of the receptacle.

As illustrated in FIG. 1, the skin testing system includes an applicator 32. In this embodiment, the applicator includes a planar member 33 having a first surface 34 that includes an upwardly projecting hand grasp or elongate handle 38. The planar member includes a second surface 36 having a plurality of picks 40. Each pick includes a base portion 41 secured within, or formed integrally with, the planar member. Preferably, the diameter of the base members corresponds to the outer diameter of the collars 14 of the testing-agent containers 12. Each pick also incudes an insert portion 42 formed integrally with the base member and having at least one skin piercing epidermal point 43 that is capable of carrying a load of testing agent. The diameter of the insert portions preferably corresponds to the inner diameter of the collars 14 of the testing-agent containers 12 so that insert portions will fit snugly into the open tops 16 defined by the collars such that a liquid tight seal is obtained. The applicator can be fabricated from extrudable or injection molded plastic and is preferably formed with a predetermined curvilinear configuration 44. Likewise, the receptacle 20 of the autoloader 11 is also formed with a curvilinear configuration 46 that corresponds to the curvilinear configuration of the applicator thereby providing positive reference orientation between the applicator and the autoloader.

As shown in FIG. 2, to load the picks 40 of the applicator 32, the applicator is positioned within the contours of the peripheral lip 27 of the receptacle 20 of the autoloader 11 to form a single unit of the combined applicator and autoloader. In this position, the insert portions 42 of the picks fit snugly into the open tops 16 defined by the collars 14 of the corresponding testing-agent containers to form a liquid tight seal. The skin testing system 10 is then inverted to allow the testing agents in the containers to immerse the points 43 of the picks so as to load each pick with an effective amount of testing agent to perform a skin test. The skin testing system is then reinverted so that the unit is upright and the applicator is removed in the loaded condition from the autoloader. The applicator is then used to deposit the testing agents epicutaneously by piercing the skin of the test subject with each pick to a predetermined depth. The testing agents are generally applied to test sites on the patient's arm or back. The pierced skin is observed for response to the testing agents.

Figures 3, 4:
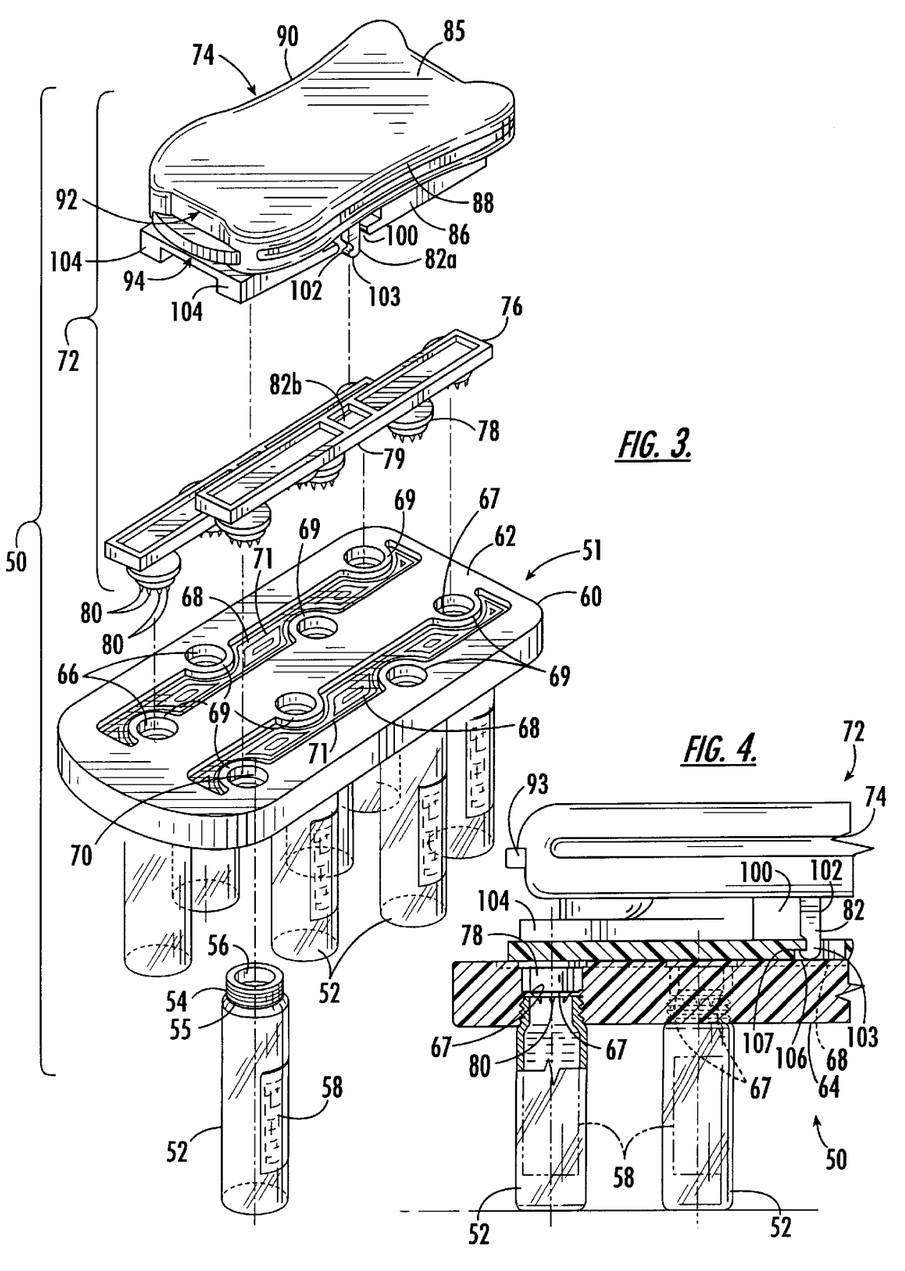
FIG. 3 is a partial exploded perspective view illustrating a second embodiment of the skin testing system of the present invention including an autoloading apparatus having a receptacle and a plurality of reservoirs and a multi-headed skin testing applicator with disposable test strips.
FIG. 4 is a fragmentary cross sectional view illustrating the skin testing system of FIG. 3.

In a second preferred embodiment, as shown in FIG. 3, the skin testing system 50 again includes an autoloader 51 and an applicator 72. The autoloader of this embodiment includes a plurality of reservoirs or testing-agent containers 52 for storing testing agents therein. As in the case of the previous embodiment, the testing-agent containers are preferably cylindrical in configuration and constructed of a nonreactive and durable material, such as an extruded or injection molded plastic or tempered glass. The containers may be pre-filled with testing agents and sealed using a removable cap or top (not shown). Each testing-agent container has a collar 54 defining an open top 56. The container preferably includes a means for labelling the container to identify the testing agent stored therein, such as a pressure-sensitive label 58.

The autoloader 51 of the second preferred embodiment also includes a receptacle 60 having first and second surfaces 62, 64 defining a plurality of apertures 66 therethrough. The apertures are preferably staggered in two groups along the length of the receptacle. As illustrated in FIG. 3, the receptacle may include two groups of four staggered apertures, each group extending along opposite sides of the receptacle for a total of eight apertures. However, it should be appreciated that the number of apertures can be as few as two or as many as desired and still be within the scope of the teachings of the present invention. Each aperture includes an aperture-reduction member 67 disposed between the first and second surfaces of the receptacle.

Each aperture 66 removably receives at least a portion of the collar 54 of one of the testing-agent containers 52. The outer surface 55 of each collar is preferably threaded. Similarly, the inner surface 70 of each aperture is correspondingly threaded from the second surface of the receptacle through to the aperture-reduction member, so that the each aperture can threadedly receive the collar of the corresponding testing-agent container. Advantageously, once the containers are secured within the apertures of the receptacle, the receptacle and containers form a free-standing autoloader unit, with the containers supporting the receptacle in the upright position.

The first surface 62 of the receptacle 60 defines at least one recess 68 that defines a rim 69 around at least a portion of each of the plurality of apertures 66 thereby inhibiting cross contamination of testing agents between the testing-agent containers 52. As illustrated in FIG. 3, the preferred embodiment includes two parallel recesses with each recess defining a rim around four of the eight apertures. Alternatively, a single recess (not shown) could encompass all of the apertures and form a rim around each of the apertures. As should be appreciated, there are many possible variations of the recess and rim structure taught by the present invention and each is considered to be within the scope of the present disclosure.

Each recess 68 preferably defines at least one rib 71 to restrict the flow of testing agents within the recess in the event any of the testing agents drip or otherwise become deposited within the recess. As shown in FIG. 3, each recess preferably includes a plurality of concentric ribs to restrict the flow of testing agents within the recesses.

As illustrated in FIG. 3, the skin testing system 50 also includes an applicator 72. In this embodiment, the applicator includes an applicator handle 74 and at least one applicator test strip 76 storable separately from the applicator handle. The test strip has a plurality of heads or picks 78. Each pick has at least one skin piercing epidermal point 80 and is capable of carrying a load of testing agent. The applicator preferably includes complimentary coupling means 82 on the applicator handle and on the test strip to permit the applicator handle to operatively pick up and releasably hold the test strip when the test strip is used.

Figure 6:
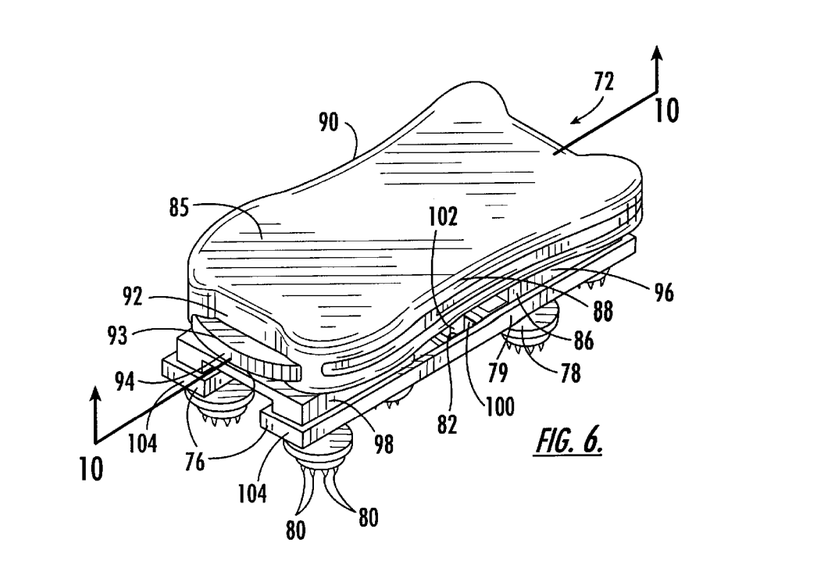
FIG. 6 is a perspective view illustrating the multi-headed skin testing applicator and disposable test strips of FIG. 3.
Figure 10:
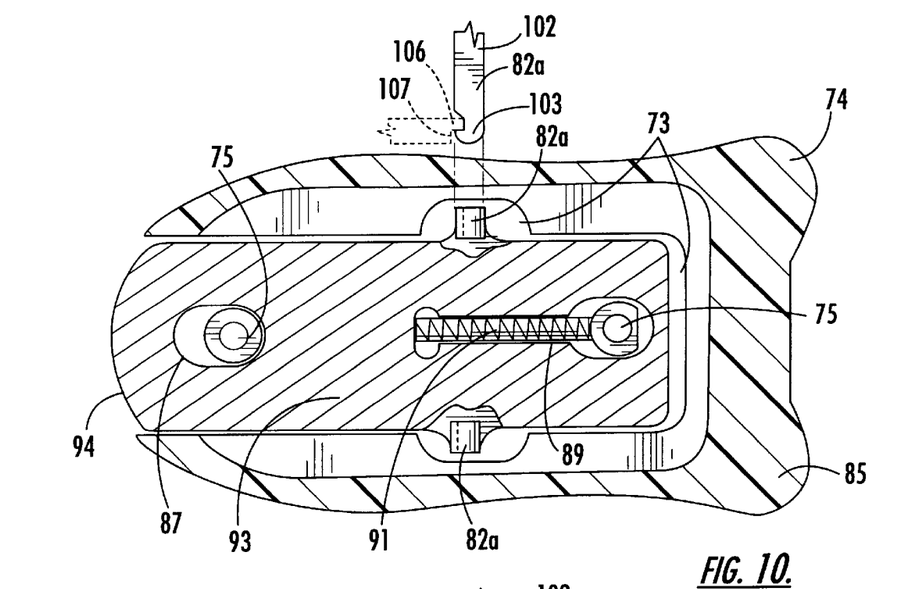
FIG. 10 is a fragmentary plan view illustrating the bottom of the multi-headed skin testing applicator of FIG. 3 with the bottom plate removed.
Figure 11:
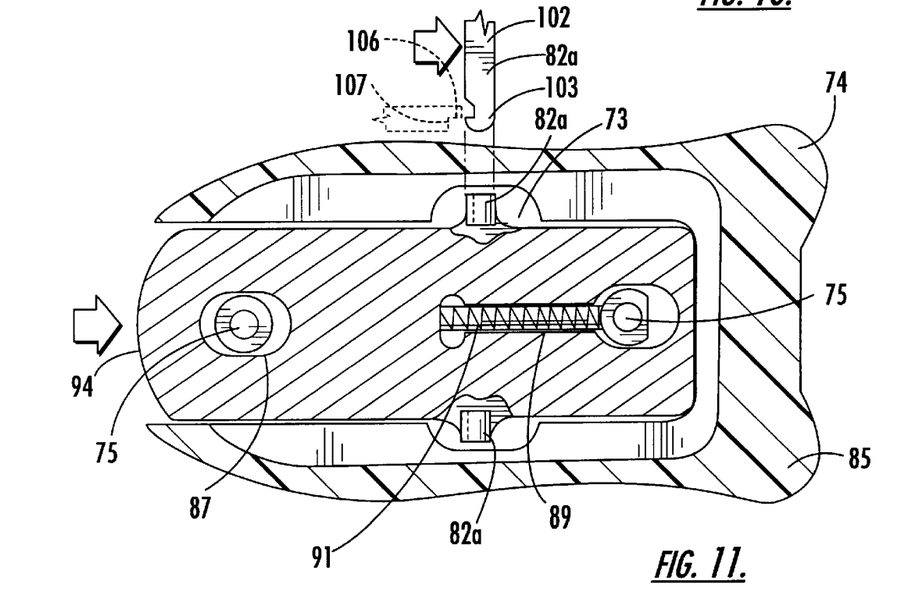
FIG. 11 is a fragmentary plan view illustrating the bottom of the multi-headed skin testing applicator of FIG. 3 with the bottom plate removed and the slide member depressed.

As shown in FIGS. 3, 4 and 6, the applicator handle 74 is of a multi-part stacked construction involving easy to assemble parts. Specifically, the applicator handle includes a top portion forming an applicator grip 85, a bottom plate 86 and a coupling means 82a for attaching and releasing the test strips 76 from the applicator handle. The grip is generally shaped to be easily accommodated by the user's hand, e.g., approximately 2 to about 3½ inches wide. The grip is held on each side 88, 90 between the user's fingers and thumb. As shown in FIGS. 10 and 11, the underside of the grip has a recessed portion 73 to accommodate the coupling means. The underside of the grip also has a pair of fastener receiving holes 75, each of which receives a threaded fastener (not shown) to secure the bottom plate 86 to the grip.

The coupling means 82a of the applicator handle 74 includes a pair of downwardly extending latches 102, a finger depressible slide member 93 linked to the latches, and a bias spring 91. As shown in FIGS. 10 and 11, the slide member is adapted to slidably fit in the recess 73 in the bottom of the grip 85, between the grip and the bottom plate 86. In addition to the downwardly extending latches, the slide member has a front edge 94, a slide hole 87 adapted to accommodate a threaded fastener (not shown) therethrough, and a second elongated fastener opening or slot 89 adapted to receive the bias spring and a second threaded fastener (not shown). As shown in FIG. 4, each of the latches has a latch tab 103 on its outer end for engagement with the forward edge 106 of the test strip opening 77. The bias spring is positioned in the slot of the slide member and is biased against the front end of the slot at one end and the fastener at the other end. The slide member extends slightly outwardly from the front of the applicator handle so that when it is depressed against the bias spring the latch tabs release each of the test strips 76.

During assembly, the grip 85 and bottom plate 86 are secured with threaded fasteners (not shown). The applicator handle 74 is assembled by securing the fasteners through the bottom plate and into the holes 75 of the grip while fitting the slide member 93 into the recess 73 on the underside of the grip with the latches 102 positioned over the openings 100 in the bottom plate. The bias spring 91 of the latch mechanism is positioned in the slot 89 in the slide member. In position, each latch will project through the corresponding opening 100 in the bottom plate so as to engage the opening 77 in the corresponding test strip 76. When assembled, the slide member will slidably be captured between the grip and the bottom plate and be biased in a forward position with the rear of the slot 89 against the fastener.

Figure 5:
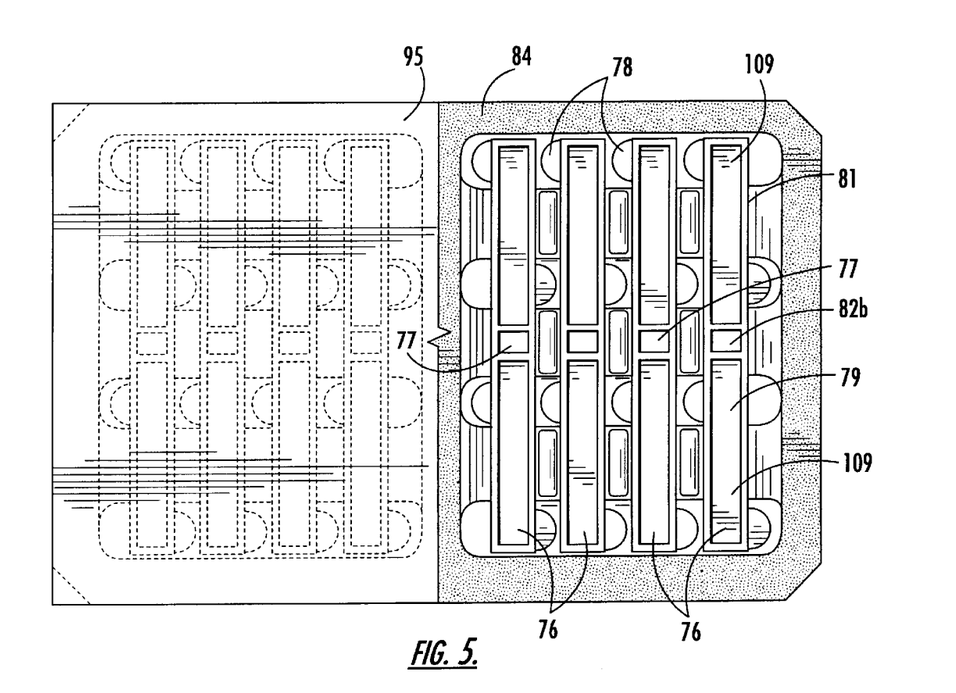
FIG. 5 is a plan view illustrating a disposable test strip package with the sterile cover removed from one compartment thus exposing a plurality of test strips.

As shown in FIG. 5, each of the test strips 76 is comprised of an elongated, relatively narrow base member 79 having a raised edge portion 81 around its outer perimeter. The test strips are preferably pre-packaged in a tray 84 having a sterile cover 95. The tray is preferably compartmentalized so that only the minimum number of sterile test strips need be exposed at any one time to avoid waste. The heads or picks 78 on the test strips each carry a plurality of scarifying points 80 that hold an effective amount of allergenic testing agent.

As illustrated in FIGS. 3 and 4, the complimentary coupling means 82b on the test strip 76 is shown by the test-strip opening 77, preferably at the mid-point of the base member 79. The forward edge of the opening 106 serves as a locking tab with the latch tab 103 of the latches 102. The width of the latches is preferably slightly narrower than the width of the test-strip opening. Preferably, the forward or locking edge 106 may include a raised stepped area 107 which permits the latch tabs 103 to more easily retain the test strip against the bottom plate 86 of the applicator handle 74.

In operation, the user grips the sides of the grip 85 and then uses the applicator handle 74 to pick up pairs of elongated sterile test strips 76 from a sterile storage tray 84, such as the one shown in FIG. 5. Specifically, the user positions applicator handle above the test strips in the tray 84 so that the latch tab 103 of each latch 102 is above a test-strip opening 77 of a corresponding test strip. The user then moves the applicator handle towards the test strips. When the latch tabs are inserted into the corresponding test-strip openings, the latch tabs will contact the forward edges 106 of the test-strip openings. As the user urges the applicator handle towards the test strips, the latch tabs are displaced away from the forward edges of the test-strip openings which pushes the slide member 93 against the bias spring 91 in the rearward direction, as shown in FIG. 11. Once the latch tabs have moved past the forward edges of the corresponding test-strip openings, the action of the bias spring forces the slide member to move forward thereby holding the front edges 106 of the test-strip openings 77 against the corresponding latch tabs 103. In the embodiment illustrated in FIG. 3, the coupling means of the applicator provides the applicator handle with the ability to pick up and hold two test strips at the same time. It will be appreciated that the coupling means on the applicator handle could as well provide for picking up just one test strip or more than two test strips.

The bottom plate 86 has an upper portion 96 that is somewhat smaller than the bottom portion 98 and serves to separate the grip 85 from the bottom portion. The bottom plate has a pair of openings 100 in the mid portion thereof for receiving the latches 102. The underside of the bottom plate has outwardly extending portions 104 that preferably fit within the recesses 109 formed on either side of the test-strip openings 77 by the raised portion 81 of the test strips. The outwardly extending portions form seats for the test strips. The bottom plate has a pair of holes (not shown) to accommodate the threaded fasteners.

Figure 7:
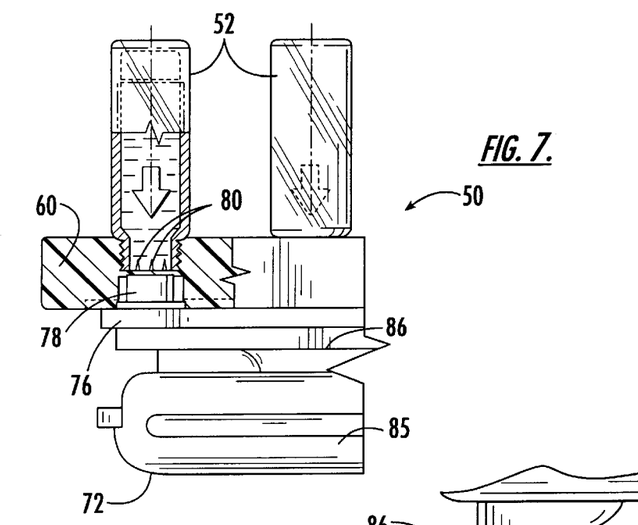
FIG. 7 is a fragmentary cross sectional view illustrating the skin testing system of FIG. 3 in the inverted position where the multiple heads are being loaded with testing agents.

As shown in FIG. 7, to load the picks 78 of the applicator 72, the applicator handle 74 is used to operatively pick up one or more test strips 76. The applicator is then positioned above the receptacle 60 of the autoloader 51 so that the picks 78 of the test strips 76 are aligned with the apertures 66 in the receptacle. As shown in FIG. 4, the applicator is then move toward the autoloader so that the picks are inserted into the apertures of the receptacle to form a single unit of the combined applicator and autoloader. Advantageously, each aperture includes an aperture-reduction member 67 disposed between the first and second surfaces 62, 64 of the receptacle. The side of each aperture-reduction member facing the first surface of the receptacle defines a chamfer that cooperates with a mating chamfer on the outer perimeter of the corresponding pick to insure that a liquid tight seal is obtained. As shown in FIG. 7, the skin test system 50 is then inverted to allow the testing agents in the containers to immerse the points 80 of the picks so as to load each pick with an effective amount of testing agent to perform a skin test. The skin testing system is then reinverted so that the unit is upright and the applicator is removed in the loaded condition from the autoloader.

Figure 8:
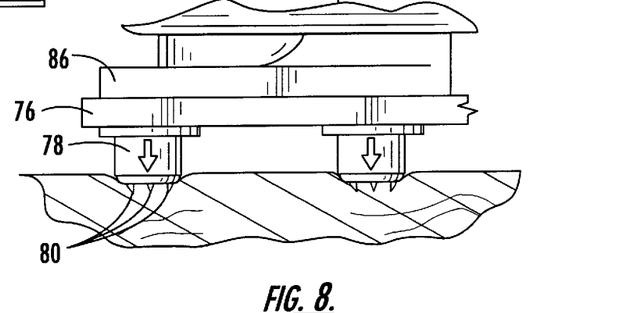
FIG. 8 is a fragmentary environmental view illustrating the application of the testing agents to the skin of a subject using the multi-headed skin testing applicator of FIG. 3.

As shown in FIG. 8, the applicator is then used to deposit the testing agents epicutaneously by piercing the skin of the test subject with each pick to a predetermined depth. The testing agents are generally applied to test sites on the patient's arm or back. The pierced skin is observed for response to the testing agents.

Figure 9:
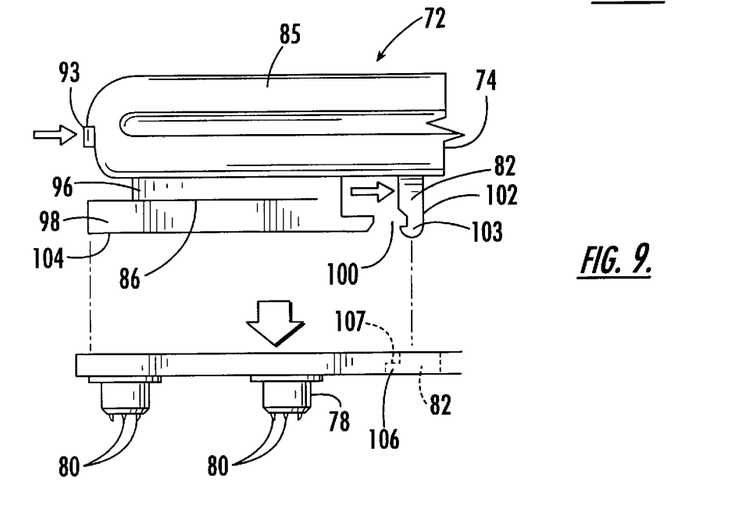
FIG. 9 is a fragmentary plan view illustrating the disposal of the test strips of the multi-headed skin testing applicator of FIG. 3.

As shown in FIG. 9, once the testing agents have been applied to the test sites using the applicator 72, the test strips 76 are disposed of by depressing the front edge 94 of the slide member 93. Specifically, the user grips the sides of the grip 85 and with a finger against the slide member front edge 94, pushes it against the bias spring 91 in a rearward motion. As illustrated in FIG. 6, the front portion 92 of the grip is somewhat indented so that the front edge 94 of the slide member 93 of the coupling means 82 extends slightly outwardly from the front edge of the grip. By pushing the slide member against the bias spring 91 in a rearward motion, the latches 102, and thus the latch tabs 103, become dislodged from the forward edge 106 of the test-strip opening 77. Advantageously, the test strips simply fall away from the applicator and may be disposed of in a biologically safe manner. The applicator is then ready to be used for subsequent skin tests.

To store the testing agents contained in the containers 52, the applicator handle 74 is used to operatively pick up one or more sterile test strips 76 from the tray 84. The picks 78 of the test strips are inserted into the corresponding apertures 66 in the receptacle 60 of the autoloader 51. In this position, the chamfer of the aperture-reduction member 67 cooperates with the mating chamfer on the outer perimeter of the corresponding pick to insure that a liquid tight seal is obtained. The applicator 72 is not removed from the autoloader thereby storing the testing agents contained in the containers and preventing contamination of the same.

While particular embodiments of the invention have been described, it will be understood, of course, that the invention is not limited thereto since modifications may be made by those skilled in the art, particularly in light of the foregoing teachings. It is therefore contemplated by the appended claims to cover any such modifications that incorporate those features of these improvements in the true spirit and scope of the invention.

That which is claimed:

1. A method for performing skin tests for biologic response, comprising:
   providing an autoloader having an applicator and a receptacle, the applicator defining a plurality of picks;
   securing a plurality of reservoirs to the receptacle of the autoloader, each of the reservoirs containing a corresponding testing agent;
   positioning the applicator adjacent the receptacle such that each of the plurality of picks of the applicator is sealably engaged by a corresponding reservoir;
   inverting the autoloader so as to load each pick with an effective amount of a corresponding testing agent;
   reinverting the autoloader to its upright position; and
   removing the applicator from the receptacle in a loaded condition ready for performing skin tests.

2. A method according to claim 1 further comprising filling each reservoir prior to said securing step.

3. A method according to claim 2 further comprising labeling each reservoir to indicate the corresponding testing agent contained therein.

4. A method according to claim 1 wherein said securing step comprises threading each reservoir into a corresponding aperture defined by the receptacle.

5. A method according to claim 1 wherein said providing step comprises securing at least one test strip to a handle to form the applicator.

6. A method according to claim 1 further comprising depositing the testing agents epicutaneously by piercing a patient's skin with each pick to a predetermined depth; and observing the pierced skin for response to the testing agents.

7. A method according to claim 6 further comprising storing the testing agents contained in the reservoirs by positioning a sterile applicator adjacent the receptacle such that each of the plurality of picks of the applicator is sealably engaged by a corresponding reservoir.

8. A method according to claim 1 wherein each of the testing agent comprises allergens selected from the group consisting of tree allergens, mold allergens, grass allergens, ragweed allergens, dust, epidermals, and weed allergens.

9. A method for performing skin tests for biologic response, comprising:
   providing an autoloader having an applicator and a receptacle, the applicator defining a plurality of picks;
   securing a plurality of reservoirs within corresponding apertures defined by the receptacle of the autoloader, each of the reservoirs containing a corresponding testing agent;
   positioning the applicator adjacent the receptacle such that each of the plurality of picks of the applicator is sealably engaged by a corresponding reservoir;
   inverting the autoloader so as to load each pick with an effective amount of a corresponding testing agent;
   reinverting the autoloader to its upright position; and
   removing the applicator from the receptacle in a loaded condition;
   depositing the testing agents epicutaneously by piercing a patient's skin with each pick to a predetermined depth; and
   observing the pierced skin for response to the testing agents.

10. A method according to claim 9 further comprising filling each reservoir prior to said securing step.

11. A method according to claim 10 further comprising labeling each reservoir to indicate the corresponding testing agent contained therein.

12. A method according to claim 9 wherein said securing step comprises threading each reservoir into the corresponding aperture defined by the receptacle.

13. A method according to claim 9 wherein said providing step comprises securing at least one sterile test strip to a handle to form the applicator.

14. A method according to claim 13 further comprising disposing of the at least one strip after said depositing step.

15. A method according to claim 9 further comprising storing the corresponding testing agent contained in each reservoir by positioning a sterile applicator adjacent the receptacle such that each of the plurality of picks of the applicator is sealably engaged by a corresponding reservoir.

16. A method according to claim 9 wherein each of the testing agent comprises allergens selected from the group consisting of tree allergens, mold allergens, grass allergens, ragweed allergens, dust, epidermals, and weed allergens.

* * * * *